(12) United States Patent
Sonnenschein et al.

(10) Patent No.: US 6,274,305 B1
(45) Date of Patent: Aug. 14, 2001

(54) INHIBITING PROLIFERATION OF CANCER CELLS

(75) Inventors: Carlos Sonnenschein; Ana M. Soto, both of Boston, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 08/769,746

(22) Filed: Dec. 19, 1996

(51) Int. Cl.$^7$ ..................................................... C12Q 1/00
(52) U.S. Cl. ............................ 435/4; 435/388; 435/405; 435/406; 435/407; 350/300; 350/326; 350/363
(58) Field of Search ................................. 435/4, 325, 388, 435/383, 404, 406, 407, 405; 530/300, 362, 363

(56) References Cited

U.S. PATENT DOCUMENTS

| | | |
|---|---|---|
| 4,859,585 | 8/1989 | Sonnenschein et al. . |
| 5,051,448 | 9/1991 | Shashoua . |
| 5,135,849 | 8/1992 | Soto et al. . |
| 5,169,862 | 12/1992 | Burke, Jr. et al. . |
| 5,192,746 | 3/1993 | Lobl et al. . |
| 5,380,712 | 1/1995 | Ballance et al. . |
| 5,539,085 | 7/1996 | Bischoff et al. . |
| 5,559,103 | 9/1996 | Gaeta et al. . |
| 5,576,423 | 11/1996 | Aversa et al. . |

FOREIGN PATENT DOCUMENTS

| | | |
|---|---|---|
| 0198745 A1 | 3/1986 | (EP) . |
| WO 95/33833 | 9/1995 | (WO) . |
| WO 95/23857 | 12/1995 | (WO) . |

OTHER PUBLICATIONS

Laursen et al., Anticancer Research 10:342–352, 1990.

Soto et al., J. Steroid Biochem. 23:87–94, 1985.

Lea et al., Anticancer Research 7:113–118, 1987.

ATCC Catalog on Line, Cell lines menu for HTB–22, 2000.

Sonnenschein et al., J. Steroid, Biochem. Molec. Biol. 59:147–154, Oct. 1996.*

Eldred et al., "Orally Active Non–Peptide Fibrinogen Receptor (GpIIb/IIIa) Antagonists: Identification of a 4–[4–[4–(Aminoiminomethyl)phenyl–1–piperazinyl]1 ]piperidineacetic Acid as a Long–Acting, Broad–Spectrum Anti–thrombotic Agent," *J. Med. Chem* 37:3882–3885 (1994).

Ku et al., "Potent Non–peptide Fibrinogen Receptor Antagonists Which Present an Alternative Pharmacophore,"*J. Med. Chem.* 38:9–12 (1995).

Lipman and Pearson, "Rapid and Sensitive Protein Similarity Searches," *Science* 227:1435–1441 (1985).

Pearson and Lipman, "Improved Tools For Biological Sequence Comparison," *Proc. Natl. Acad. Sci. USA* 85:2444–2448 (1988).

Furuya et al., "Mechanisms of Estrogen Action on the Proliferation of MCF–7 Human Breast Cancer Cells in n Improved Culture Medium," *Cancer Research* 49:6670–6674 (1989).

Soto et al., "A Plasma–Borne Specific Inhibitor of the Proliferation of Human Estrogen–Sensitive Breast Tumor Cells (Estrocolyone–I)," *J. Steroid Biochem. Molec. Biol.* 43:703–712 (1992).

Savu et al., "Mouse $\alpha_1$–Fetoprotein and Albumin," *J. Biol. Chem.* 256:9414–9418 (1981).

Quirk, et al., "Production of Recombinant Human Serum Albumin from *Saccharomyces cerevisiae*," *Biotechnology and Applied Biochemistry* 11:273–287 (1989).

Murby, et al., "Differential Degradation of a Recombinant Albumin–Binding Receptor in *Escherchia coli*," *Eur. J. Biochem* 0199:41–46 (1991).

Fitos, et al., "Binding Studies with Recombinant Human Serum Albumin Obtained by Expression of a Synthetic Gene in Yeast: Steroselective Binding and Allosteric Interaction with Benzodiazepine and Coumarin Ligands," *Biochemical Pharmacology* 46:1159–1163 (1993).

Baker, "Conservation of Amino Acid Sequences in Albumin: Is Albumin an Essential Protein?," *Mol. Biol. Evol.* 1:321–323 (1989).

Meloun, et al., "Complete Amino Acid Sequence of Human Serum Albumin," *FEBS Letters* 58:134–137 (1975).

Latta, et al., "Synthesis and Purification of Mature Human Serum Albumin from *E. Coli*," *Biotechnology* 5:1309–1314 (1987).

Fleer, et al., "Stable Mutlible Vectors for High–level Secretion of Recombinant Human Serum Albumin by Kluyveromyces yeasts," *Biotechnology* 9:968–975 (1991).

Sleep et al., "The Secretion of Human Serum Albumin from the Yeast *Saccharomyces cerevisiae* using five Different Leader Sequences," *Biotechnology* 8:42–46 (1990).

* cited by examiner

*Primary Examiner*—Sheela Huff
*Assistant Examiner*—Larry R. Helms
(74) *Attorney, Agent, or Firm*—Medlen & Carroll, LLP

(57) ABSTRACT

A method of testing cancer cells is described. Assays are provided for determining the potential for inhibiting cancer cells proliferation using albumin-derived peptides. The methods of the present invention allow for drug screening as well as for evaluation of biopsied tumors.

13 Claims, 10 Drawing Sheets

Asp Ala His Lys Ser Glu Val Ala His Arg Phe Lys Asp Leu Gly Glu Glu Asn Phe Lys
                                                                              20
                     10
Ala Leu Val Leu Ile Ala Phe Ala Gln Tyr Lou Gln Gln Cys Pro Phe Glu Asp His Val
                     30                                                       40
Lys Leu Val Asn Glu Val Thr Glu Phe Ala Lys Thr Cys Val Ala Asp Glu Ser Ala Glu
                     50                                                       60
Asn Cys Asp Lys Ser Leu His Thr Leu Phe Gly Asp Lys Leu Cys Thr Val Ala Thr Leu
                     70                                                       80
Arg Glu Thr Tyr Gly Glu Met Ala Asp Cys Cys Ala Lys Gln Glu Pro Glu Arg Asn Glu
                     90                                                      100
Cys Phe Leu Gln His Lys Asp Asp Asn Pro Asn Leu Pro Arg Leu Val Arg Pro Glu Val
                    110                                                      120
Asp Val Met Cys Thr Ala Phe His Asp Asn Glu Glu Thr Phe Leu Lys Lys Tyr Leu Tyr
                    130                                                      140
Glu Ile Ala Arg Arg His Pro Tyr Phe Tyr Ala Pro Glu Leu Leu Phe Phe Ala Lys Arg
                    150                                                      160

FIG. 1

180
Tyr Lys Ala Ala Phe Thr Glu Cys Cys Gln Ala Ala Asp Lys Ala Ala Cys Leu Leu Pro

200
Lys Leu Asp Glu Leu Arg Asp Glu Gly Lys Ala Ser Ser Ala Lys Gln Arg Leu Lys Cys

220
Ala Ser Leu Gln Lys Phe Gly Glu Arg Ala Phe Lys Ala Trp Ala Val Ala Arg Leu Ser

240
Gln Arg Phe Pro Lys Ala Glu Phe Ala Glu Val Ser Lys Leu Val Thr Asp Leu Thr Lys

260
Val His Thr Glu Cys Cys His Gly Asp Leu Leu Glu Cys Ala Asp Asp Arg Ala Asp Leu

280
Ala Lys Tyr Ile Cys Glu Asn Gln Asp Ser Ile Ser Ser Lys Leu Lys Glu Cys Cys Glu

300
Lys Pro Lou Leu Glu Lys Ser His Cys Ile Ala Glu Val Glu Asn Asp Glu Met Pro Ala

320
Asp Leu Pro Ser Leu Ala Ala Asp Phe Val Glu Ser Lys Asp Val Cys Lys Asn Tyr Ala

FIG. 1

330
Glu Ala Lys Asp Val Phe Leu Gly Met Phe Leu Tyr Glu Tyr Ala Arg Arg His Pro Asp
                                                                            340

350
Tyr Ser Val Val Leu Leu Arg Leu Ala Lys Thr Tyr Glu Thr Thr Leu Glu Lys Cys
                                                                   360

370
Cys Ala Ala Ala Asp Pro His Glu Cys Tyr Ala Lys Val Phe Asp Glu Phe Lus Pro Leu
                                                                        380

390
Val Glu Glu Pro Gln Asn Leu Ile Lys Gln Asn Cys Glu Leu Phe Glu Gln Leu Gly Glu
                                                                        400

410
Tyr Lys Phe Gln Asn Ala Leu Leu Val Arg Tyr Thr Lys Lys Val Pro Gln Val Ser Thr
                                                                        420

430
Pro Thr Leu Val Glu Val Ser Arg Asn Leu Gly Lys Val Gly Ser Lys Cys Cys Lys His
                                                                        440

450
Pro Glu Ala Lys Arg Met Pro Cys Ala Glu Asp Tyr Leu Ser Val Val Leu Asn Gln Leu
                                                                        460

470
Cys Val Leu His Glu Lys Thr Pro Val Ser Asp Arg Val Thr Lys Cys Cys Thr Glu Ser
                                                                        480

FIG. 1

490
Leu Val Asn Arg Arg Pro Cys Phe Ser Ala Leu Glu Val Asp Glu Thr Tyr Val Pro Lys
500

510
Glu Phe Asn Ala Glu Thr Phe Thr Phe His Ala Asp Ile Cys Thr Leu Ser Glu Lys Glu
520

530
Arg Gln Ile Lys Lys Gln Thr Ala Leu Val Glu Leu Val Lys His Lys Pro Lys Ala Thr
540

550
Lys Glu Gln Leu Lys Ala Val Met Asp Asp Phe Ala Ala Phe Val Glu Lys Cys Cys Lys
560

570
Ala Asp Asp Lys Glu Thr Cys Phe Ala Glu Glu Gly Lys Lys Leu Val Ala Ala Ser Gln
580

Ala Ala Leu Gly Leu

FIG. 1

```
        10          20          30          40          50          60          70          80
GATGCACACAAGAGTGAGGTTGCTCTCATCGGTTTAAAGATTTGGGAGAAGAAATTTCAAAGCCTTGGTGTTGATTGCCTT
 D  A  H  K  S  E  V  A  H  R  F  K  D  L  G  E  E  N  F  K  A  L  V  L  I  A  F 90         100         110         120         130         140         150         160
TGCTCAGTATCTTCAGCAGTGTCCATTTGAAGATCATGTGAAATTAGTGAATGAAGTAACTGAATTTGCAAAAACATGTG
 A  Q  Y  L  Q  Q  C  P  F  E  D  H  V  K  L  V  N  E  V  T  E  F  A  K  T  C 170         180         190         200         210         220         230         240
TTGCTGATGAGTCAGCTGAAAATTGTGACAAATGCACTTCATACCCTTTTTGGAGACAAATTATGCACAGTTGCAACTCTT
 V  A  D  E  S  A  E  N  C  D  K  S  L  H  T  L  F  G  D  K  L  C  T  V  A  T  L 250         260         270         280         290         300         310         320
CGTGAAACCTATGGTGAAATGGCTGACTGCTGTGCAAAACAAGAACCTGAGAGAAATGCTTCTTGCAACACAAAGA
 R  E  T  Y  G  E  M  A  D  C  C  A  K  Q  E  P  E  R  N  E  C  F  L  Q  H  K  D 330         340         350         360         370         380         390         400
TGACAACCCAAACCTCCCCCGATTGGTGAGACCAGAGGTTGATGTGATGTGCACTGCTTTTCATGACAATGAAGAGACAT
 D  N  P  N  L  P  R  L  V  R  P  E  V  D  V  M  C  T  A  F  H  D  N  E  E  T 410         420         430         440         450         460         470         480
TTTTGAAAAATACTTATATGAAATTGCCAGAAGACATCCTTACTTTTTATGCCCGGAACTCCTTTTCTTTGCTAAAAGG
 F  L  K  K  Y  L  Y  E  I  A  R  R  H  P  Y  F  Y  A  P  E  L  L  F  F  A  K  R 490         500         510         520         530         540         550         560
TATAAAGCTGCTTTTACAGAATGTTGCCAAGCTGCTGATAAAGCTGCCTGTTGCCAAAGCTCGATGAACTTCGGGA
 Y  K  A  A  F  T  E  C  C  Q  A  A  D  K  A  A  C  L  L  P  K  L  D  E  L  R  D
```

FIG. 2

```
         570              580              590              600              610              620              630              640
TGAAGGGAAGGCTTCGTCTGCCAAATGTGCCAGTCTCCAAAAATTTGGAGAAAGAGCTTTCAAAGCAT
 E  G  K  A  S  S  A  K  Q  R  L  K  C  A  S  L  Q  K  F  G  E  R  A  F  K  A 650              660              670              680              690              700              710              720
GGGCAGTGGCTCGCCCTGAGCCAGAGATTTCCCAAAGCTGAGTTTGCAGAAGTTTCCAAGCTTAGTGACAGATCTTACCAAA
 W  A  V  A  R  L  S  Q  R  F  P  K  A  E  F  A  E  V  S  K  L  V  T  D  L  T  K 730              740              750              760              770              780              790              800
GTCCACACGGAATGCTGCCATGGAGATCTGCTTGAATGTGCTGATGACAGGGCGGACCTTGCCAAGTATATCTGTGAAAA
 V  T  E  C  C  H  G  D  L  L  E  C  A  D  D  R  A  D  L  A  K  Y  I  C  E  N 810              820              830              840              850              860              870              880
TCAGGATTCGATCTCCAGTAAACTGAAGGAATGCTGTGAAAAACCTCTGTTGGAAAATCCCACTGCATTGCCGAAGTGG
 Q  D  S  I  S  S  K  L  K  E  C  C  E  K  P  L  L  E  K  S  H  C  I  A  E  V 890              900              910              920              930              940              950              960
AAAATGATGAGATGCCTGCTGACTTGCCTTCATTAGCTGCTGATTTTGTTGAAAGTAAGGATGTTTGCAAAAACTATGCT
 E  N  D  E  M  P  A  D  L  P  S  L  A  A  D  F  V  E  S  K  D  V  C  K  N  Y  A 970              980              990             1000             1010             1020             1030             1040
GAGGCAAAGGATGTCTTCCTGGGCATGTTTTTGTATGAATATGCAAGAAGGCATCCTGATTACTCTGTCGTGCTGCTGCT
 E  A  K  D  V  F  L  G  M  F  L  Y  E  Y  A  R  R  H  P  D  Y  S  V  V  L  L  L
```

FIG. 2

```
                1050       1060       1070       1080       1090       1100       1110       1120
          GAGACTTGCCAAGACATATGAAACCACTCTAGAGAAGTGCTGTGCCGCTGCAGATCCTCATGAATGCTATGCCAAAGTGT
           R  L  A  K  T  Y  E  T  T  L  E  K  C  C  A  A  A  D  P  H  E  C  Y  A  K  V 1130       1140       1150       1160       1170       1180       1190       1200
          TCGATGAATTTAAACCTCTCTGTGGAAGAGCCTCAGAATTTAATCAAACAAACTGTGAGCTTTTTGAGCAGCTTGGAGAG
           F  D  E  F  K  P  L  V  E  E  P  Q  N  L  I  K  Q  N  C  E  L  F  E  Q  L  G  E 1210       1220       1230       1240       1250       1260       1270       1280
          TACAAATTCCAGAATGCGCTATTAGTTCGTTACACCCCAAGTGTCAACTCCAACTCCACTCCTTGTAGAGGTCTC
           Y  K  F  Q  N  A  L  L  V  R  Y  T  K  K  V  P  Q  V  S  T  P  T  L  V  E  V  S 1290       1300       1310       1320       1330       1340       1350       1360
          AAGAAACCTAGGAGAAAAGTGGGCAGCAAATGTTGTAAACATCCTGAAGCAAAAAGAATGCCCTGTGCAGAAGACTATCTAT
           R  N  L  G  K  V  G  S  K  C  C  K  H  P  E  A  K  R  M  P  C  A  E  D  Y  L 1370       1380       1390       1400       1410       1420       1430       1440
          CCGTGGTCCTGAACCAGTTATGTGTGTTGCATGAGAAAACGCCAGTAAGTGACAGAGTCACAAAATGCTGCACAGAGTCC
           S  V  V  L  N  Q  L  C  V  L  H  E  K  T  P  V  S  D  R  V  T  K  C  C  T  E  S 1450       1460       1470       1480       1490       1500       1510       1520
          TTGGTGAACAGGCGACCATGCTTTCAGCTCTCAGCTCTTGAAGTCGATGATGAAACATACGTTCCCAAAGAGTTTAATGCTGAAACATT
           L  V  N  R  R  P  C  F  S  A  L  E  V  D  E  T  Y  V  P  K  E  F  N  A  E  T  F
```

FIG. 2

```
            1530      1540      1550      1560      1570      1580      1590      1600
CACCTTCCATGCAGATATATGCCACACTTTCTGAGAAGGAGAGACAAATCAAGAAACTGCACTTGTTGAGCTTGTGA
 T  F  H  A  D  I  C  T  L  S  E  K  E  R  Q  I  K  K  Q  T  A  L  V  E  L  V 1610      1620      1630      1640      1650      1660      1670      1680
AACACAAGCCCAAGGCAACAAAGAGCAACTGAAAGCTGTGTTATGGATGATTTCGCAGCTTTTGTAGAGAAGTGCTGCAAG
 K  H  K  P  K  A  T  K  E  Q  L  K  A  V  M  D  D  F  A  A  F  V  E  K  C  C  K 1690      1700      1710      1720      1730      1740      1750      1760
GCTGACGATAAGGAGACCTGCTTTGCCGAGGAGGGTAAAAAACTTGTTGCTGCAAGTCAAGCTGCCTTAGGCTTATAACA
 A  D  D  K  E  T  C  F  A  E  E  G  K  K  L  V  A  A  S  Q  A  A  L  G  L 1770      1780
TCTACATTTAAAAGCATCTCAG
```

FIG. 2

INHIBITING PROLIFERATION OF CANCER CELLS

This application was made with government support under CA13410 awarded by the National Institutes of Health and DCB-8711746 awarded by the National Science Foundation. The government has certain rights in the invention.

FIELD OF THE INVENTION

The invention generally relates to the inhibition of cancer cell proliferation, and, more specifically, to the testing of cancer cells for their ability to be inhibited, and to the identification and use of drugs to inhibit cancer cell proliferation.

BACKGROUND

The term "chemotherapy" simply means the treatment of disease with chemical substances. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman *The Pharmacological Basis of Therapeutics* (Pergamon Press, 8th Edition) (pp. 1209–1216).

What is needed is a specific anticancer approach that is particularly suitable for specific cancer cells. Importantly, the treatment must be effective with minimal host toxicity.

SUMMARY OF THE INVENTION

The invention generally relates to the inhibition of cancer cell proliferation, and, more specifically, to the testing of cancer cells for their ability to be inhibited, and to the identification and use of drugs to inhibit cancer cell proliferation. The present invention provides A) an in vitro model for testing cancer cells and evaluating their potential for being inhibited, B) a screening assay for identifying drugs that inhibit cancer cell proliferation, and C) chemotherapeutics for inhibiting cancer cell proliferation in vivo.

A variety of assay formats are contemplated for testing the potential for inhibiting cancer cells. In one embodiment, a portion of a patient's tumor is obtained (e.g., by biopsy) and placed in tissue culture. Thereafter, the response of the cancer cells to a albumin-derived peptide is assessed. Where the albumin-derived peptide inhibits proliferation, the tumor can be considered to be expressing the corresponding plasma membrane receptor and such a tumor may be suitable for chemotherapeutics that target this receptor. The potential for reversing or overcoming this inhibition with hormone (e.g. estradiol) can also be assessed by adding the hormone to the culture. Where the inhibition with the albumin-derived peptide is cancelled by the presence of the hormone, the tumor can be considered to be expressing the corresponding plasma membrane hormone-binding receptor and such a tumor may be suitable for chemotherapeutics that target this particular receptor. Moreover, other therapies may be adopted that those skilled in the art recognize to be appropriate for "hormone sensitive" tumors.

In one embodiment, the present invention contemplates a method of evaluating human cancer comprising: a) providing i) a human cancer patient, and ii) an albumin-derived peptide; b) obtaining cancer cells from said patient; c) contacting said cells ex vivo with said albumin-derived peptide; and d) measuring cancer cell proliferation. Preferably the cancer cells are cultured in serum-free culture media so as to essentially avoid introducing complicating factors. In another embodiment, the present invention provides a method of testing human cancer cells comprising: a) providing i) a human cancer patient, ii) an albumin-derived peptide, and iii) one or more hormones or hormone analogues; b) obtaining cancer cells from said patient; c) culturing said cells in serum-free culture media in the presence of said albumin-derived peptide and said one or more hormones or hormone analogues; and d) measuring cancer cell proliferation.

As noted above, the present invention also contemplates a screening assay for identifying drugs that inhibit tumor invasion. The present invention contemplates a screening assay utilizing the binding activity of albumin-derived peptides. In one embodiment, cancer cells (whether obtained from a primary tumor or grown as an established cell line) are placed in tissue culture in the presence of an albumin-derived peptide. It is contemplated that an inhibitable tumor cells cultured in the presence of the albumin-derived peptide will not proliferate. In the drug screening assay, candidate drug inhibitors are added to a second tissue culture containing the inhibitable tumor cells (this can be done individually or in mixtures). Where the inhibitable cells are found to be similarly inhibited by the candidate drug, a drug inhibitor is indicated (hereinafter a "type 1 drug inhibitor"). It is also contemplated that the drug screening be done in the presence of a blocking hormone, i.e. a hormone that overcomes or cancels the inhibition caused by the albumin-derived peptide. For example, where the inhibition by the albumin-derived peptide is cancelled by the addition of estradiol, a candidate drug can be added in an attempt to interfere with the action of the hormone. Where the presence of estradiol does not result in proliferation, a second type of drug inhibitor is indicated (hereinafter a "type 2 drug inhibitor"). It is not intended that the present invention be limited by the nature of the drugs screened in the screening assay of the present invention. A variety of drugs, including peptides, are contemplated. Antibodies to albumin, the hormone or the corresponding receptors are contemplated as convenient positive controls.

In one embodiment, the present invention contemplates a method of screening drugs comprising: a) providing: i) albumin-inhibitable tumor cells, ii) an inhibitor selected from the group consisting of albumin, an albumin-derived peptide, and an albumin-derived peptide analogue, iii) one or more steroid hormones, and iv) a candidate drug; b) contacting said cells in vitro with said inhibitor, said one or more steroid hormones and said candidate drug; and c) measuring the extent of tumor cell proliferation.

It is not intended that the present invention be limited by the means by which the extent of proliferation is measured. A variety of quantitative and qualitative means is known in the art, including (but not limited to): 1) the uptake of radiolabelled nucleic acid precursors (e.g. tritiated thymidine), 2) microscopic examination, and 3) automated cell counting (including lysing cells and counting nuclei).

It is not intended that the present invention be limited by the nature of the cancer cells used for drug screening. Both i) cancer cells from established cancer cell lines and ii) cancer cells obtained from patients (e.g. from a biopsy) are contemplated. A variety of tumor types are contemplated as well, including, but not limited to, breast cancer cells and prostate cancer cells.

Finally, the present invention contemplates chemotherapeutics for treating cancer in vivo. In one embodiment, the present invention contemplates chemotherapeutics to inhibit cancer cell proliferation. Both type 1 and type 2 drug inhibitors identified through the above-described screening assay are contemplated. Moreover, albumin-derived peptides and peptide analogues are specifically contemplated for in vivo use. In one embodiment, the method comprises administering an albumin-derived peptide or peptide analogue as adjunct therapy with additional chemotherapeutics.

DESCRIPTION OF THE FIGURES

FIG. 1 (SEQ ID NO: 2) shows an amino acid sequence representative of human serum albumin.

FIG. 2 (SEQ ID NO: 1) depicts the DNA sequence coding for mature HSA.

DEFINITIONS

Figure 3:
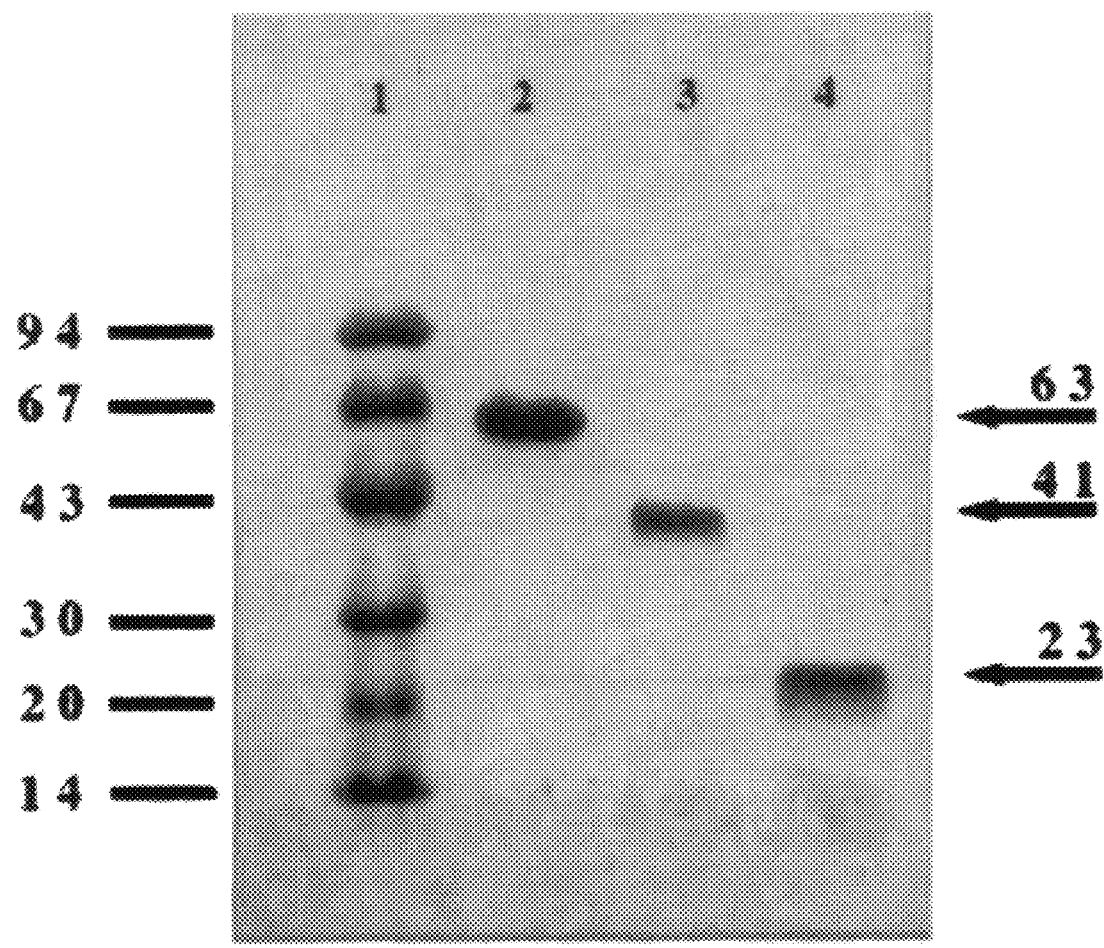
FIG. 3 shows the SDS-PAGE results for albumin and albumin-derived peptides.

The term "drug" as used herein, refers to any medicinal substance used in humans or other animals. Encompassed within this definition are naturally occurring and synthetic organic compounds, as well as naturally occurring and synthetic recombinant pharmaceuticals (whether hormones, peptides or peptide analogues).

The term "hormone" refers to trace substances produced by various endocrine glands which serve as chemical messengers carried by the blood to various target organs, where they regulate a variety of physiological and metabolic activities in vertebrates. The steroid hormones include the estrogens, or female sex hormones, the androgens, or male hormones (testosterone, dihydrotestosterone); the progestational hormone progesterone; and the steroid hormones of the adrenal cortex (major forms, cortisol, aldosterone, and corticosterone).

The term "albumin-derived peptide" refers to a peptide having a sequence that is identical to a portion of the amino acid sequence of albumin. The present invention also contemplates analogues. In one embodiment, an "albumin-derived peptide analogue" comprises a peptide having a sequence that is similar (but not identical) to a portion of the amino acid sequence of albumin. In another embodiment, an "albumin-derived peptide analogue" is a "mimetic." Mimetics are compounds mimicking the necessary conformation for recognition and docking to the receptor binding to the albumin-derived peptide.

The term "receptors" refers to structures expressed by cells and which recognize binding molecules (e.g. ligands).

The term "antagonist" refers to molecules or compounds which inhibit the action of a "native" or "natural" compound (such as albumin). Antagonists may or may not be homologous to these natural compounds in respect to conformation, charge or other characteristics. Thus, antagonists may be recognized by the same or different receptors that are recognized by the natural compound.

The term "host cell" refers to any cell which is used in any of the screening assays of the present invention. "Host cell" also refers to any cell which either naturally expresses particular receptors of interest or is genetically altered so as to produce these normal or mutated receptors.

DESCRIPTION OF THE INVENTION

As noted above, chemotherapeutic agents are currently employed to reduce the unrestricted growth of cancer cells. However, better agents are needed that more specific and less toxic. The invention generally relates to the inhibition of cancer cell proliferation, and, more specifically, to the testing of cancer cells for their ability to be inhibited, and to the identification and use of drugs to inhibit cancer cell proliferation.

A. Assays for Inhibiting Cancer Cell Proliferation

Discovering how to inhibit the proliferation of tumor cells first requires the development of assays with which to test the potential for tumor cells to be inhibited. The present invention contemplates a variety of in vitro assays involving the use of albumin and/or albumin-derived peptides.

Albumin and Making Albumin-Derived Peptides

In one assay system, the present invention contemplates using albumin and/or albumin-derived peptides. Human serum albumin (HSA) is the most abundant plasma protein. A molecule of HSA consists of a single non-glycosylated polypeptide chain of 585 amino acids of formula molecular weight 66,500. A representative amino acid sequence of HSA is shown in FIG. 1 (SEQ ID NO: 2). Variations in the sequence are known. As used herein, "variants of human serum albumin" are those sequence showing greater than 80% homology, and preferably greater than 90% homology, and most preferably greater than 95% homology, to the sequence set forth in FIG. 1.

Albumin-derived peptides are those peptides having a sequence that is identical to a portion of the amino acid sequence of albumin as set forth in FIG. 1 (SEQ ID NO: 2). In one embodiment, the present invention contemplates an albumin-derived peptide comprising the N-terminal portion of human serum albumin up to amino acid residue n, where n is between 360 and 430, are more preferably between 369 and 419.

In one embodiment, an "albumin-derived peptide analogue" comprises a peptide having a sequence that is similar (but not identical) to a portion of the amino acid sequence of albumin as set forth in FIG. 1 (SEQ ID NO: 2). Such similar sequences are contemplated to have conservative substitutions and/or deletions and/or additions.

Conservative substitutions are those where one or more amino acids are substituted for others having similar properties in the understanding of one skilled in the art. Typical substitutions include, but are not limited by, substitutions of alanine or valine for glycine, arginine or asparagine for glutamine, serine for threonine and histidine for lysine.

Analogues having deletions are those having up to ten (and preferably only one or two) amino acid residues lacking (in comparison to the sequence set forth in FIG. 1 (SEQ ID NO: 2). Preferably, such deletions occur in the portion between 1 and 370, and more preferably between 100 and 369.

Analogues having additions are those peptides that encompass additional amino acid residues, including whole sequences which are not native to HSA. In one embodiment, the peptide analogue having additions comprises a peptide between one hundred and five hundred amino acids in length. In one embodiment, the peptide analogue having additions comprises additional amino acids added to the amino terminus of an albumin-derived sequence. In one embodiment, the peptide analogue having additions comprises additional amino acids added to the carboxy terminus of an albumin-derived sequence. In another embodiment, the peptide analogue having additions comprises additional amino acids added to both the amino and carboxy termini.

One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic albumin-derived peptide analogues are those peptides with statistically significant sequence homology and similarity (Z value of Lipman and Pearson algorithm in Monte Carlo analysis exceeding 6).

Preferred albumin-derived peptides include, but are limited to, HSA (1–373) (i.e. where the C-terminal amino acid is Val); HSA (1–387) (i.e. where the C-terminal amino acid is Leu); HSA (1–388) (i.e. where the C-terminal amino acid is Ile); HSA (1–379) (i.e. where the C-terminal amino acid is Lys); HSA (1–390) (i.e. where the C-terminal amino acid is Gln); and HSA (1–407) (i.e. where the C-terminal amino acid is Leu).

It is not intended that the present invention be limited by the manner in which the albumin-derived peptide is made. In one embodiment, the peptide is made by enzymatic digestion. For example, a trypsin-like enzyme will cleave HSA between Lys (389) and Gln (390), as well as at other sites. In another embodiment, the peptide is made by peptide synthesis. In still another embodiment, Albumin-derived peptides are conveniently made by recombinant techniques. See U.S. Pat. No. 5,380,712, hereby incorporated by reference. FIG. 2 (SEQ ID NO: 1) depicts the DNA sequence coding for mature HSA. This sequence can be used together with standard recombinant DNA procedures to construct expression vectors for the expression of albumin-derived peptides.

It is not intended that the present invention be limited by the precise amount of albumin or albumin-derived peptide used in the assays of the present invention. When albumin is used, the inhibiting concentration of albumin is typically between one microgram and two milligram per milliliter of culture fluid, and more preferably greater than one hundred micrograms per milliliter and less than one milligram per milliliter.

B. Drug Screening Assays

As noted above, the present invention also contemplates a screening assay for identifying drugs that inhibit cancer cell proliferation. The present invention contemplates a screening assay utilizing the binding activity of albumin and/or albumin-derived peptides, including but not limited to the above-described peptides. In one embodiment, an inhibitable tumor cell line is placed in tissue culture. The tumor cells (under ordinary conditions) will proliferate; however, in the presence of albumin and/or albumin-derived peptides, the cell proliferation will be inhibited.

In the drug screening assay of the present invention, candidate drug inhibitors are added to the tissue culture (this can be done individually or in mixtures). Where the cancer cells are found to be inhibited, a drug inhibitor is indicated.

It is not intended that the present invention be limited by the nature of the drugs screened in the screening assay of the present invention. A variety of drugs, including peptides, are contemplated.

It is also not intended that the present invention be limited by the particular tumor cells used for drug testing. A variety of tumor cells (for both positive and negative controls) are contemplated (including but not limited to the cells set forth in Table 1 below). In addition, primary tumor cells from patients are contemplated.

Where the inhibitable cells are found to be similarly inhibited by the candidate drug, a drug inhibitor is indicated (hereinafter a "type 1 drug inhibitor"). It is also contemplated that the drug screening be done in the presence of a blocking hormone, i.e. a hormone that overcomes or cancels the inhibition caused by the albumin-derived peptide. Where the presence of a hormone does not result in proliferation, a second type of drug inhibitor is indicated (hereinafter a "type 2 drug inhibitor"). It is not intended that the present invention be limited by the nature of the hormone used in conjunction with the drug screening assay. As discussed below, the present invention contemplates hormones mediating cell proliferation.

Hormones Mediating Proliferation of Cancer Cells

While an understanding of the mechanisms involved in cancer is not necessary to the successful practice of the present invention, it is believed that hormones can mediate the proliferation of cancer cells. The present invention contemplates the use of steroid sex hormones in conjunction with the assays for testing cancer cells.

TABLE 1

Designation And Origin Of Human Cell Lines And Strains[1]

| ORIGIN | CELL LINES OR STRAINS |
|---|---|
| Colonic carcinoma | SW1116, HCT116, SKCO-1, HT-29, KM12C, KM12SM, KM12L4, SW480 |
| Pancreatic carcinoma | BxPC-3, AsPC-1, Capan-2, MIA PaCa-2, Hs766T |
| Colon adenoma | VaCo 235 |
| Lung carcinoma | A549 |
| Prostate carcinoma | PC-3, DU-145 |
| Breast cancer | 009P, 013T, MCF-7, MDA-MB231 |
| Lymphoma | Daudi, Raji |
| Breast epithelium | 006FA |
| Diploid fibroblast | HCS (human corneal stroma), MRC-5 |

[1]The SW1116, HT-29, SW480, Raji lymphoblastoid cells, and the pancreatic lines are obtained from the American Type Culture Collection.

Naturally occurring or endogenous estrogens constitute one class of steroid sex hormones which are produced in the ovaries and other tissues in the body. The naturally occurring estrogens are estrone (also known as $E_1$), estradiol-17B (also known as $E_2$), and estriol (also known as $E_3$). Synthetic compounds having estrogenic properties include ethinyl estradiol (Estinyl); 3-methyl-ethinyl estradiol (Mestranol); and diethylstilbestrol (DES); methallenestril (Vallestril); and doisynoestrol (Fenocylin).

The present invention contemplates testing the response of the cancer cells to albumin and albumin-derived peptides. Where the albumin-derived peptide inhibits proliferation, the tumor can be considered to be expressing the corresponding plasma membrane receptor and such a tumor may be suitable for chemotherapeutics that target this receptor. The potential for reversing or overcoming this inhibition with hormone (e.g. estradiol) can also be assessed by adding the hormone to the culture. Where the inhibition with the albumin-derived peptide is cancelled by the presence of the hormone, the tumor can be considered to be expressing the corresponding plasma membrane hormone-binding receptor and such a tumor may be suitable for chemotherapeutics that target this particular receptor. Moreover, other therapies may be adopted that those skilled in the art recognize to be appropriate for "hormone sensitive" tumors.

A variety of formats and protocols for testing hormones is contemplated. Illustrative formats and protocols are described in U.S. Pat. Nos. 4,859,585 and 5,135,849, both of which are hereby incorporated by reference.

C. Administering Chemotherapeutics

It is contemplated that albumin, albumin-derived peptides, and albumin-derived peptide analogues, as well as the type 1 and type 2 drugs discussed above, can be administered systemically or locally to inhibit tumor cell proliferation in cancer patients. They can be administered intravenously, intrathecally, intraperitoneally as well as orally. Moreover, they can be administered alone or in combination with anti-proliferative drugs.

Where combinations are contemplated, it is not intended that the present invention be limited by the particular nature of the combination. The present invention contemplates combinations as simple mixtures as well as chemical hybrids. An example of the latter is where the peptide or drug is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antagonists of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

Designing Mimetics

It may be desirable to administer an analogue of an albumin-derived peptide. As mentioned previously, the present invention contemplates compounds mimicking the necessary conformation for recognition and docking to the albumin receptor. A variety of designs for such mimetics are possible. For example, cyclic peptides, in which the necessary conformation for binding is stabilized by nonpeptides, are specifically contemplated. U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all hereby incorporated by reference, describe multiple methods for creating such compounds.

Synthesis of nonpeptide compounds that mimic peptide sequences is also known in the art. Eldred et al., (*J. Med. Chem.* 37:3882 (1994)) describe nonpeptide antagonists that mimic the Arg-Gly-Asp sequence. Likewise, Ku et al., (*J. Med. Chem.* 38:9 (1995)) give further elucidation of the synthesis of a series of such compounds. Such nonpeptide compounds are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexyl-carbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); mAb (monoclonal antibody); MW (molecular weight); PBS (phosphate buffered saline); U (units); d(days).

A clonal population of the human breast cancer MCF-7 cell line was used in some of the experiments described below. These cells were routinely grown in 5% fetal bovine serum (FBS) supplemented-Dulbecco's Modified Eagle's Medium (DME). Charcoal-dextran (CD) stripped serum-supplemented medium inhibits their proliferation and estradiol cancels this effect. Estrogen non-target, serum-insensitive human breast cancer MDA-MB231 cells (ATCC, Rockville, Md.) were used as controls; they were grown under the same conditions as MCF-7 cells.

Recombinant human albumin (rHA), recombinant Domain I (aa 1–194, rDI) and Domain I+II (aa 1–387, rDI+II) were obtained from Delta Biotechnology Ltd., Nottingham, U.K. rHA and truncated HA transcripts were produced in yeast grown in synthetic medium comprising sucrose, vitamins and inorganic salts.

At chosen intervals after exposure to 2 mg/ml rHA with or without 100 pM estradiol, cells were trypsinized, pelleted by centrifugation at 100 g for 3 min, resuspended in 10% DMSO-10% CDHuS and snap frozen. Cells were kept at $-20°$ C. for up to 7 days. Cells were quickly thawed at 37° C., centrifuged and resuspended at a density of $10^6$ cells/ml in a solution containing 0.1% Triton X-100, 0.1 mg/ml propidium iodide (PI) (Sigma) in DME. Total DNA was quantified by propidium iodide binding. The RNAse treatment used in the original method to hydrolyze double stranded RNA did not significantly affect the DNA fluorescence and was omitted. Cells were analyzed in a Becton-Dickinson FACSCAN flow cytometer. Ten thousand cells were collected for each point. Data were collected and compiled with Becton-Dickinson Lysis II and Cell Fit software.

HA-free serum was obtained by Cibracron Blue and by hexyl-S agarose chromotography. Ten milliliters of CD stripped serum were dialyzed against start buffer [500 mM NaCl, 500 mM $K_2SO_4$, 50 mM sodium phosphate buffer (SPB) pH 7.6 containing 10 $\mu$M butylated hydroxytoluene (BHT)] and chromatographed through a 1.6×12 cm hexyl-S agarose column. After extensive elution of the breakthrough proteins, the retained fraction (HA) was eluted first with 50 mM SPB, pH 7.6, containing 10 $\mu$M BHT, and finally with 40% ethylene glycol in 50 mM SPB, pH 7.6, containing 10 $\mu$M BHT. Removal of HA was monitored electrophoretically and by immunoblots. The three hexyl-S agarose fractions were dialyzed against a buffer suitable for tissue culture (100 mM NaCl, 25 mM Hepes, pH 7.4, containing 1 $\mu$M BHT) and their effect on cell proliferation tested at concentrations ranging from 0.25 to mg/ml of protein in ITDME.

In some experiments, serum and recombinant proteins were analyses by 1D-sodium dodecylsulphate-polyacrylamide gel electrophoresis (SDS-PAGE) using 12.5% homogeneous and 10–15% gradient polyacrylamide gels and SDS buffer strips in the electrophoresis Phast System (Pharmacia, Piscataway, N.J.). Gels were stained with Coomassie blue. Gel images were digitized and analyses using the BioImage, whole band software package (Millipore Corp., Bedford, Mass.).

A polyclonal antibody was obtained in rabbits using as antigen serum albumin (Sigma; cat. no. A1887); it was purified by chromatography through tandem columns of butyl-S and hexyl-S agarose as described by Porath. The immunoglobulin fraction was precipitated with 2.2 M ($NH_4$)$_2SO_4$, dialyzed and purified by affinity chromatography using as immunoadsorbant rHA coupled to CNBr-activated Sepharose-4B. A monoclonal mouse anti-HA IgG (Sigma; cat. no. A6684) and a polyclonal anti-HA serum (cat. no. 126582, lot 703293) supplied by Calbiochem (Richmond, Calif.) gave similar results. However, the monoclonal antibody was the most sensitive one; as little as 0.5 mg HA/lane were clearly resolved as a band by the BioImage software. Serum proteins were resolved by SDS-PAGE, transferred electrophoretically onto Immobilon-P membranes using the Phast System (ID-PAGE). Membranes were blocked with 60 mg/l teleostean gelatin, reacted with the monoclonal antibody (1:20000), rinsed, and processed with a VEctastain ABC-Ap kit (Vector, Inc., Burlingame, Calif.) for reaction with the second antibody and alkaline phosphatase following the protocol, described by the manufacturer. Immunoreactive bands were visualized after incubation with the substrate [5-bromo-1-chloro-3-indolyl phosphate/nitroblue tetrazolium BCIP/NBT substrate kit (Vector)].

EXAMPLE 1

Inhibitory Effects of Albumin

To assess the inhibitory effect of serum or purified protein preparations, $4\times10^4$ cells/well were seeded in 12-well Falcon Multiplates in 5% FBS; they were allowed to attach for 24 h before exposing them to test medium. Cell proliferation yields were measured after 4 days in DME plus 25 $\mu$g transferrin (T)/ml and 100 ng insulin (I)/ml (TTDME) alone, or ITDME plus CD human serum (CDHuS), or purified protein preparations. Each sample was tested in duplicate in the presence or absence of 100 pM estradiol ($E_2$) and each experiment was repeated at least three times. Phenol red-free media were used in all experiments involving cell proliferation rates or yields. Cells were lysed and nuclei counted on a Coulter Counter Model ZM. Estrogens were removed from serum, HA (Sigma Chemical Co.; cat. no. A1887) and from rHA preparations by CD stripping.

Figure 4:
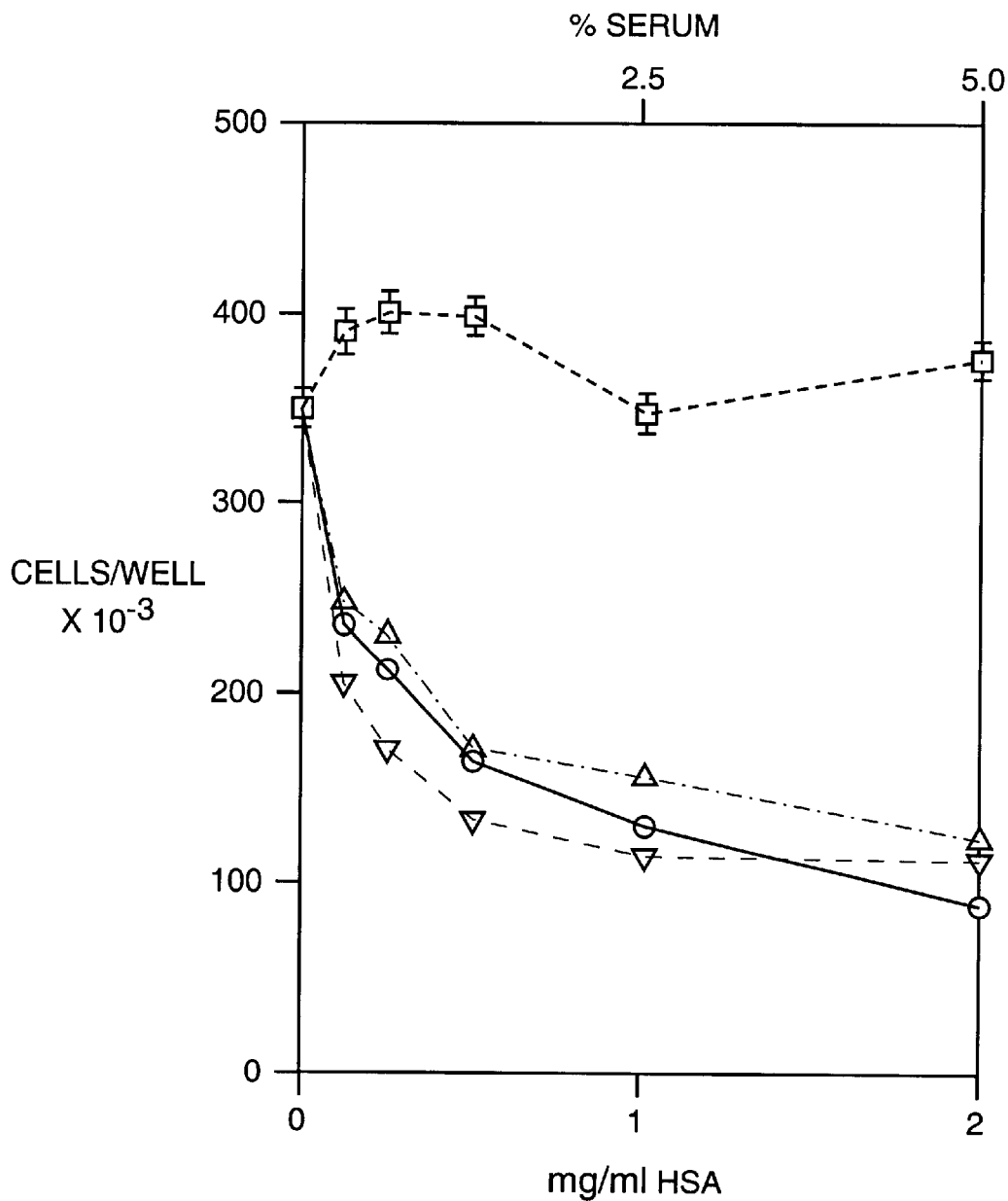
FIG. 4 is a graph showing the dose response of cancer cells to albumin in the presence and absence of estradiol.

As seen in FIG. 4, CDHuS (open diamonds) and CDHA (open circles) inhibited the proliferation of MCF-7 cells in a dose-dependent manner; similarly, rHA (closed diamonds) inhibited the proliferation of these cells. Estradiol (closed squares) reversed the inhibitory effect. Progesterone, 5α-dihydrotestosterone, the synthetic androgen R1881, hydrocortisone, and thyroxine failed to reverse the effect of rHA (data not shown).

EXAMPLE 2

Inhibitory Activity of Truncated Forms of rHA

To assess whether the inhibitory activity of albumin was encoded in a specific sequence within the albumin molecule, the inhibitory effect of truncated peptides encoding the first domain alone and the first and second domains (see FIG. 3) was tested in the manner that rHA was tested in Example 1.

The inhibitory activity of dDI+II was comparable to that of rHA; rDI also showed inhibitory activity, albeit quantitatively lower than that of rHA or rDI+II, both when expressed as a molar concentration and as mg/ml (data not shown).

EXAMPLE 3

Conjugation of Albumin-derived Peptides

In this example, the preparation of a peptide conjugate is described. As noted above, the albumin-derived peptides of the present invention can be made synthetically or recombinantly. A cysteine can be added to facilitate conjugation to other proteins.

In order to prepare a protein for conjugation, it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS") available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM $NaPO_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

From the above, it should be clear that the present invention provides a method of testing of cancer cells, and in particular identifying cancer cells that are inhibitable as well as hormone sensitive. With regard to the later, distinguishing such tumors the physician to change and/or optimize therapy. Importantly, the albumin-derived peptides of the present invention (and other drugs developed by use of the screening assay of the present invention) will provide treatment associated with minimal host toxicity.

What is claimed is:

1. A method of measuring human cancer cell proliferation, comprising:
  a) providing:
    i) a human cancer patient,
    ii) an albumin-derived peptide, wherein said albumin-derived peptide is truncated in length, thereby shorter than the 585 amino acid long human serum albumin, and comprises domains I and II of human serum albumin;
  b) obtaining cancer cells from said patient;
  c) culturing said cancer cells in serum-free media;
  d) contacting said cells ex vivo with said albumin-derived peptide; and
  e) measuring the extent of cancer cell proliferation.

2. The method of claim 1, wherein said cancer cells are obtained from a biopsy.

3. The method of claim 1, wherein said cancer cells are selected from the group consisting of breast cancer cells and prostate cancer cells.

4. The method of claim 1, wherein said albumin-derived peptide consists of the amino acids 1–387 of human serum albumin.

5. The method of claim 1, wherein said albumin-derived peptide consists of the amino acids 1–388 of human serum albumin.

6. A method of measuring human cancer cell proliferation, comprising:
  a) providing:
    i) a human cancer patient,
    ii) an albumin-derived peptide, wherein said albumin-derived peptide is truncated, thereby shorter in length than the 585 amino acid long human serum albumin, and comprises domains I and II of human serum albumin; and
    iii) one or more hormones or hormone analogues;
  b) obtaining cancer cells from said patient;
  c) culturing said cells in serum-free culture media in the presence of said albumin-derived peptide and said one or more hormones or hormone analogues; and
  d) measuring cancer cell proliferation.

7. The method of claim 6, wherein said cancer cells are obtained from a biopsy.

8. A The method of claim 6, wherein said cancer cells are selected from the group consisting of breast cancer cells and prostate cancer cells.

9. The method of claim 6, wherein said hormone comprises an estrogen.

10. The method of claim 6, wherein said albumin-derived peptide consists of domains I and II of human serum albumin.

11. The method of claim 6, wherein said albumin-derived peptide consists of the amino acids 1–387 of human serum albumin.

12. The method of claim 6, wherein said albumin-derived peptide consists of the amino acids 1–388 of human serum albumin.

13. A method of measuring human cancer cell proliferation, comprising:
  a) providing:
    i) a human cancer patient,
    ii) an albumin-derived peptide, said peptide consisting of the N-terminal region of the 585 amino acid sequence of human serum albumin, said N-terminal region having the same amino acid sequence as said human serum albumin up to and including a terminal amino acid selected from the group consisting of amino acids 360–430 of said human serum albumin;
  b) obtaining cancer cells from said patient;
  c) culturing said cancer cells in serum-free media;
  d) contacting said cells ex vivo with said albumin-derived peptide; and
  e) measuring the extent of cancer cell proliferation.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..1755

(xi) SEQUENCE DESCRIPTION: SEQ ID NO:1:

```
GAT GCA CAC AAG AGT GAG GTT GCT CAT CGG TTT AAA GAT TTG GGA GAA        48
Asp Ala His Lys Ser Glu Val Ala His Arg Phe Lys Asp Leu Gly Glu
 1               5                  10                  15

GAA AAT TTC AAA GCC TTG GTG TTG ATT GCC TTT GCT CAG TAT CTT CAG        96
Glu Asn Phe Lys Ala Leu Val Leu Ile Ala Phe Ala Gln Tyr Leu Gln
                20                  25                  30

CAG TGT CCA TTT GAA GAT CAT GTA AAA TTA GTG AAT GAA GTA ACT GAA       144
Gln Cys Pro Phe Glu Asp His Val Lys Leu Val Asn Glu Val Thr Glu
            35                  40                  45

TTT GCA AAA ACA TGT GTT GCT GAT GAG TCA GCT GAA AAT TGT GAC AAA       192
Phe Ala Lys Thr Cys Val Ala Asp Glu Ser Ala Glu Asn Cys Asp Lys
        50                  55                  60

TCA CTT CAT ACC CTT TTT GGA GAC AAA TTA TGC ACA GTT GCA ACT CTT       240
Ser Leu His Thr Leu Phe Gly Asp Lys Leu Cys Thr Val Ala Thr Leu
 65                  70                  75                  80

CGT GAA ACC TAT GGT GAA ATG GCT GAC TGC TGT GCA AAA CAA GAA CCT       288
Arg Glu Thr Tyr Gly Glu Met Ala Asp Cys Cys Ala Lys Gln Glu Pro
                85                  90                  95

GAG AGA AAT GAA TGC TTC TTG CAA CAC AAA GAT GAC AAC CCA AAC CTC       336
Glu Arg Asn Glu Cys Phe Leu Gln His Lys Asp Asp Asn Pro Asn Leu
                100                 105                 110

CCC CGA TTG GTG AGA CCA GAG GTT GAT GTG ATG TGC ACT GCT TTT CAT       384
Pro Arg Leu Val Arg Pro Glu Val Asp Val Met Cys Thr Ala Phe His
            115                 120                 125

GAC AAT GAA GAG ACA TTT TTG AAA AAA TAC TTA TAT GAA ATT GCC AGA       432
Asp Asn Glu Glu Thr Phe Leu Lys Lys Tyr Leu Tyr Glu Ile Ala Arg
        130                 135                 140

AGA CAT CCT TAC TTT TAT GCC CCG GAA CTC CTT TTC TTT GCT AAA AGG       480
Arg His Pro Tyr Phe Tyr Ala Pro Glu Leu Leu Phe Phe Ala Lys Arg
145                 150                 155                 160

TAT AAA GCT GCT TTT ACA GAA TGT TGC CAA GCT GCT GAT AAA GCT GCC       528
Tyr Lys Ala Ala Phe Thr Glu Cys Cys Gln Ala Ala Asp Lys Ala Ala
```

-continued

```
                       165                 170                 175
TGC CTG TTG CCA AAG CTC GAT GAA CTT CGG GAT GAA GGG AAG GCT TCG         576
Cys Leu Leu Pro Lys Leu Asp Glu Leu Arg Asp Glu Gly Lys Ala Ser
            180                 185                 190

TCT GCC AAA CAG AGA CTC AAA TGT GCC AGT CTC CAA AAA TTT GGA GAA         624
Ser Ala Lys Gln Arg Leu Lys Cys Ala Ser Leu Gln Lys Phe Gly Glu
        195                 200                 205

AGA GCT TTC AAA GCA TGG GCA GTG GCT CGC CTG AGC CAG AGA TTT CCC         672
Arg Ala Phe Lys Ala Trp Ala Val Ala Arg Leu Ser Gln Arg Phe Pro
    210                 215                 220

AAA GCT GAG TTT GCA GAA GTT TCC AAG TTA GTG ACA GAT CTT ACC AAA         720
Lys Ala Glu Phe Ala Glu Val Ser Lys Leu Val Thr Asp Leu Thr Lys
225                 230                 235                 240

GTC CAC ACG GAA TGC TGC CAT GGA GAT CTG CTT GAA TGT GCT GAT GAC         768
Val His Thr Glu Cys Cys His Gly Asp Leu Leu Glu Cys Ala Asp Asp
                245                 250                 255

AGG GCG GAC CTT GCC AAG TAT ATC TGT GAA AAT CAG GAT TCG ATC TCC         816
Arg Ala Asp Leu Ala Lys Tyr Ile Cys Glu Asn Gln Asp Ser Ile Ser
            260                 265                 270

AGT AAA CTG AAG GAA TGC TGT GAA AAA CCT CTG TTG GAA AAA TCC CAC         864
Ser Lys Leu Lys Glu Cys Cys Glu Lys Pro Leu Leu Glu Lys Ser His
        275                 280                 285

TGC ATT GCC GAA GTG GAA AAT GAT GAG ATG CCT GCT GAC TTG CCT TCA         912
Cys Ile Ala Glu Val Glu Asn Asp Glu Met Pro Ala Asp Leu Pro Ser
    290                 295                 300

TTA GCT GCT GAT TTT GTT GAA AGT AAG GAT GTT TGC AAA AAC TAT GCT         960
Leu Ala Ala Asp Phe Val Glu Ser Lys Asp Val Cys Lys Asn Tyr Ala
305                 310                 315                 320

GAG GCA AAG GAT GTC TTC CTG GGC ATG TTT TTG TAT GAA TAT GCA AGA        1008
Glu Ala Lys Asp Val Phe Leu Gly Met Phe Leu Tyr Glu Tyr Ala Arg
                325                 330                 335

AGG CAT CCT GAT TAC TCT GTC GTG CTG CTG CTG AGA CTT GCC AAG ACA        1056
Arg His Pro Asp Tyr Ser Val Val Leu Leu Leu Arg Leu Ala Lys Thr
            340                 345                 350

TAT GAA ACC ACT CTA GAG AAG TGC TGT GCC GCT GCA GAT CCT CAT GAA        1104
Tyr Glu Thr Thr Leu Glu Lys Cys Cys Ala Ala Ala Asp Pro His Glu
        355                 360                 365

TGC TAT GCC AAA GTG TTC GAT GAA TTT AAA CCT CTT GTG GAA GAG CCT        1152
Cys Tyr Ala Lys Val Phe Asp Glu Phe Lys Pro Leu Val Glu Glu Pro
    370                 375                 380

CAG AAT TTA ATC AAA CAA AAC TGT GAG CTT TTT GAG CAG CTT GGA GAG        1200
Gln Asn Leu Ile Lys Gln Asn Cys Glu Leu Phe Glu Gln Leu Gly Glu
385                 390                 395                 400

TAC AAA TTC CAG AAT GCG CTA TTA GTT CGT TAC ACC AAG AAA GTA CCC        1248
Tyr Lys Phe Gln Asn Ala Leu Leu Val Arg Tyr Thr Lys Lys Val Pro
                405                 410                 415

CAA GTG TCA ACT CCA ACT CTT GTA GAG GTC TCA AGA AAC CTA GGA AAA        1296
Gln Val Ser Thr Pro Thr Leu Val Glu Val Ser Arg Asn Leu Gly Lys
            420                 425                 430

GTG GGC AGC AAA TGT TGT AAA CAT CCT GAA GCA AAA AGA ATG CCC TGT        1344
Val Gly Ser Lys Cys Cys Lys His Pro Glu Ala Lys Arg Met Pro Cys
        435                 440                 445

GCA GAA GAC TAT CTA TCC GTG GTC CTG AAC CAG TTA TGT GTG TTG CAT        1392
Ala Glu Asp Tyr Leu Ser Val Val Leu Asn Gln Leu Cys Val Leu His
    450                 455                 460

GAG AAA ACG CCA GTA AGT GAC AGA GTC ACA AAA TGC TGC ACA GAG TCC        1440
Glu Lys Thr Pro Val Ser Asp Arg Val Thr Lys Cys Cys Thr Glu Ser
465                 470                 475                 480

TTG GTG AAC AGG CGA CCA TGC TTT TCA GCT CTG GAA GTC GAT GAA ACA        1488
```

```
Leu Val Asn Arg Arg Pro Cys Phe Ser Ala Leu Glu Val Asp Glu Thr
            485                 490                 495

TAC GTT CCC AAA GAG TTT AAT GCT GAA ACA TTC ACC TTC CAT GCA GAT      1536
Tyr Val Pro Lys Glu Phe Asn Ala Glu Thr Phe Thr Phe His Ala Asp
        500                 505                 510

ATA TGC ACA CTT TCT GAG AAG GAG AGA CAA ATC AAG AAA CAA ACT GCA      1584
Ile Cys Thr Leu Ser Glu Lys Glu Arg Gln Ile Lys Lys Gln Thr Ala
        515                 520                 525

CTT GTT GAG CTT GTG AAA CAC AAG CCC AAG GCA ACA AAA GAG CAA CTG      1632
Leu Val Glu Leu Val Lys His Lys Pro Lys Ala Thr Lys Glu Gln Leu
        530                 535                 540

AAA GCT GTT ATG GAT GAT TTC GCA GCT TTT GTA GAG AAG TGC TGC AAG      1680
Lys Ala Val Met Asp Asp Phe Ala Ala Phe Val Glu Lys Cys Cys Lys
545                 550                 555                 560

GCT GAC GAT AAG GAG ACC TGC TTT GCC GAG GAG GGT AAA AAA CTT GTT      1728
Ala Asp Asp Lys Glu Thr Cys Phe Ala Glu Glu Gly Lys Lys Leu Val
                565                 570                 575

GCT GCA AGT CAA GCT GCC TTA GGC TTA TAACATCTAC ATTTAAAAGC            1775
Ala Ala Ser Gln Ala Ala Leu Gly Leu
                580                 585

ATCTCAG                                                              1782

(2) INFORMATION FOR SEQ ID NO:2:

(i) SEQUENCE CHARACTERISTICS:
        (A) LENGTH: 585 amino acids
        (B) TYPE: amino acid
        (D) TOPOLOGY: linear (ii) MOLECULE TYPE: protein (xi) SEQUENCE DESCRIPTION: SEQ ID NO:2:

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205
```

-continued

```
Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575

Ala Ala Ser Gln Ala Ala Leu Gly Leu
                580                 585
```